United States Patent
Kirchhoff et al.

(10) Patent No.: US 11,446,482 B2
(45) Date of Patent: Sep. 20, 2022

(54) INTRAVASCULAR BLOOD PUMP

(71) Applicant: Abiomed Europe Gmbh, Aachen (DE)

(72) Inventors: Frank Kirchhoff, Aachen (DE); Thorsten Siess, Aachen (DE); Wolfgang Kerkhoffs, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 10 days.

(21) Appl. No.: 16/980,686

(22) PCT Filed: Mar. 21, 2019

(86) PCT No.: PCT/EP2019/057165
§ 371 (c)(1),
(2) Date: Sep. 14, 2020

(87) PCT Pub. No.: WO2019/180179
PCT Pub. Date: Sep. 26, 2019

(65) Prior Publication Data
US 2021/0015981 A1  Jan. 21, 2021

(30) Foreign Application Priority Data

Mar. 23, 2018 (EP) .................................... 18163763

(51) Int. Cl.
*A61M 60/122* (2021.01)
*A61M 60/818* (2021.01)
(Continued)

(52) U.S. Cl.
CPC ........ *A61M 60/818* (2021.01); *A61M 60/135* (2021.01); *A61M 60/148* (2021.01); *A61M 60/205* (2021.01); *A61M 60/242* (2021.01); *A61M 60/416* (2021.01); *A61M 60/829* (2021.01); *A61M 2205/103* (2013.01); *A61M 2205/3606* (2013.01)

(58) Field of Classification Search
CPC .. A61M 60/205; A61M 1/101; A61M 60/135; A61M 60/818; A61M 2205/103
See application file for complete search history.

(56) References Cited

U.S. PATENT DOCUMENTS 5,613,935 A  3/1997 Jarvik
5,713,730 A  2/1998 Nose et al.
(Continued)

FOREIGN PATENT DOCUMENTS

EP  0961621 A1  12/1999

OTHER PUBLICATIONS

Extended European Search Report dated Aug. 28, 2018 for corresponding EP Appl. No. 18163763.8 (5 pages).
(Continued)

*Primary Examiner* — Michael J D'Abreu
(74) *Attorney, Agent, or Firm* — Botos Churchill IP Law LLP

(57) ABSTRACT

An intravascular blood pump having a rotatable shaft carrying an impeller and a housing with an opening through which the shaft extends with the impeller positioned outside the housing. The shaft and the housing have surfaces forming a circumferential gap which converges towards the impeller-side end of the gap and which has a minimum gap width of preferably no more than 5 μm, more preferably no more than 2 μm.

15 Claims, 5 Drawing Sheets

(51) Int. Cl.
    *A61M 60/829*     (2021.01)
    *A61M 60/148*     (2021.01)
    *A61M 60/135*     (2021.01)
    *A61M 60/205*     (2021.01)
    *A61M 60/416*     (2021.01)
    *A61M 60/242*     (2021.01)

(56) References Cited

U.S. PATENT DOCUMENTS

| | | |
|---|---|---|
| 2001/0041934 A1 | 11/2001 | Yamazaki et al. |
| 2009/0093796 A1 | 4/2009 | Pfeffer et al. |
| 2013/0102834 A1 | 4/2013 | Kaneshima et al. |
| 2015/0051436 A1* | 2/2015 | Spanier ............... A61M 60/135 600/16 |
| 2017/0340791 A1 | 11/2017 | Aboul-Hosn et al. |

OTHER PUBLICATIONS

PCT International Search Report and Written Opinion for PCT/EP2019/057165 dated Jun. 25, 2019 (12 pages).
Office Action in corresponding Singapore Patent Application No. 11202006725T dated Mar. 28, 2022 (5 pp.).

* cited by examiner

INTRAVASCULAR BLOOD PUMP

CROSS-REFERENCE TO RELATED APPLICATIONS

The present application is a national phase entry under 35 U.S.C. § 371 of International Application No. PCT/EP2019/057165, filed Mar. 21, 2019, published as International Publication No. WO 2019/180179 A1, which claims priority from European Patent Application No. 18163763.8, filed Mar. 28, 2018, all of which are incorporated herein by reference.

BACKGROUND OF INVENTION

This invention relates to an intravascular blood pump, in particular a percutaneously insertable blood pump, for supporting blood circulation in human or optionally also animal bodies. For instance, the blood pump may be designed to be inserted percutaneously into a femoral artery and guided through the body's vascular system in order, for example, to support or replace the pumping action in the heart.

A blood pump of the afore-mentioned type is known e.g. from EP 0 961 621 B1 which possesses a drive section, a catheter attached to the proximal end of the drive section (which is the end of the drive section closer to the doctor or "rear end" of the drive section) and having lines extending there through for the power supply to the drive section, and a pump section fastened at the distal end of the drive section. The drive section comprises a motor housing having an electric motor disposed therein, with the motor shaft of the electric motor distally protruding out of the drive section and into the pump section. The pump section in turn comprises a tubular pump housing having an impeller rotating therein which is seated on the end of the motor shaft protruding out of the motor housing. The motor shaft is mounted in the motor housing in two bearings which are maximally removed from each other in order to guarantee a true, exactly centered guidance of the impeller within the pump housing. While a radial ball bearing is used for the bearing at the proximal end of the motor housing, the impeller-side bearing, which is the bearing closest to the blood, is configured as a shaft seal against the blood made of polytetrafluoroethylene which has a high hardness and a low coefficient of friction so as to provide a bearing and at the same time prevent blood from entering the motor housing through such distal bearing. The entry of blood into the motor housing is furthermore counteracted by a purge fluid being passed through the motor housing and the impeller-side shaft seal bearing. This is done at a purge fluid pressure that is higher than the pressure present in the blood.

An improvement of the aforementioned blood pump is disclosed in US 2015/0051436 A1 and shown in FIG. 2 attached hereto. Here, the impeller-side bearing at the distal end of the motor housing comprises an axial sliding bearing and a radial sliding bearing or a combined axial-radial sliding bearing, wherein the radial sliding bearing replaces the aforementioned shaft seal bearing. Accordingly, the purge fluid passes through the gap of the impeller-side radial sliding bearing so as to prevent blood from entering into the housing.

While the present invention will be described and is preferably used in context with the aforementioned type of intravascular blood pump having a motor contained in said housing, the present invention is likewise advantageously applicable in other types of intravascular blood pumps where the motor is outside the patient's body and the rotational energy for the impeller is transmitted through the catheter and said housing attached to the distal end of the catheter by means of a flexible rotating drive cable. Also in this type of intravascular blood pumps, a purge fluid is usually passed into the patient's blood through an opening through which the drive shaft extends.

A general problem arises with the heparin that is typically mixed into the purge fluid. That is, despite the purge fluid flowing through the gap formed between the shaft and the opening of the housing, thereby pushing back the blood which tends to enter the housing through such gap, blood ingress into the gap cannot entirely be prevented. In particular, some blood may always enter at least into a distal section of such gap. Heparin helps to prevent coagulation of the blood in the gap or adhesion of blood to the surfaces and, thus, prevents blockage of shaft rotation. However, doctors often do not want heparin to be administered to the patient's blood via the purge fluid. For instance, during first aid, heparin may be counterproductive as it prevents the coagulation of blood and, thus, healing or hemostasis. Also, the amount of heparin administered to the patient's blood along with the purge fluid is difficult to control for various reasons. In particular, the amount of heparin is often more than what is desired by the doctors. Accordingly, doctors would often prefer to supply heparin to the patient separate from the operation of the blood pump, if and in the amount needed.

Accordingly, there is a need for an intravascular blood pump which can run, if desired, with a purge fluid that contains no or at least less heparin.

SUMMARY OF INVENTION

Therefore, according to a first aspect of the invention, an intravascular blood pump may comprise a rotatable shaft carrying an impeller and a housing having an opening, wherein the shaft extends through the opening with the impeller positioned outside said housing, the shaft and the housing having surfaces forming a circumferential gap within said opening. This is no different than the prior art discussed above, and said gap may in particular constitute a radial sliding bearing for the shaft. However, in the blood pump disclosed herein, the gap converges towards the front end or impeller-side end such that a minimum width of the gap is located somewhere within 50% of the length of the gap closest to the impeller-side end of the gap. More preferably, said minimum width is present at least at the impeller-side end of the gap.

The advantage of a gap converging towards the front end or impeller-side end or distal end of the gap, these terms having the same meaning, consists in that a pressure drop arising in a purge fluid flowing along the length of the gap from proximal to distal can be kept low as compared to a pressure drop in a non-converging gap of the same length having said minimum width over the entire length of the gap. More specifically, it is desired according to the invention to have a relatively high speed of the purge fluid at the impeller-side end of the gap, which is the side of the gap which comes in contact with blood, to prevent blood from entering into the gap. Thus, the smaller the gap the better it is. However, very small gaps along the entire length of the gap require that the purge fluid is delivered to the blood pump with an extremely high pressure. By making the gap convergent towards the distal end, purge fluid pumps offering a pressure of e.g. 1 to 1.5 bar may be used even with a very small minimum gap width.

For instance, a minimum gap of 5 µm in the area of the impeller-side end of the gap may allow the purge fluid to exit the gap with such a high speed that substantially no blood will enter into the gap. Accordingly, it becomes possible to purge the gap with a purge fluid having relatively little or even no heparin.

The minimum gap width of 5 µm or less also provides to a certain extent a physical barrier against ingress of red blood cells into the gap, because of the relatively large blood cell diameter of approximately 8 µm. However, since the thickness of blood cells is only approximately 2 µm, it is preferred that the minimum gap width is 2 µm or less. As stated, due to the even smaller gap widths, purge fluid flows through the gap at an even higher speed, thereby pushing the blood back out of the gap with the highest possible kinetic energy.

In the case that the minimum gap width is actually limited to the impeller-side end of the gap, i.e. limited to an infinitesimal short section of the length of the gap, this may lead to increased wear in the respective section of the gap. Therefore, according to a preferred embodiment, the section of the gap with minimum gap width may extend over 50% or less, preferably 30% or less, of the length of the gap, but preferably not less than 20% of the length of the gap, in order to keep the wear low. A length of such section may be in the range of between 0.1 and 0.7 mm, more preferably between 0.2 and 0.4 mm.

The convergence of the gap may be realized by a taper of one or both surfaces forming the gap, i.e. a tapering outer surface of the gap formed by the inner surface of the opening through the wall of the housing and a tapering inner surface of the gap formed by the surface of the shaft. A taper of the outer surface of the gap means a decrease of the diameter of the wall opening towards the impeller-side end of the gap, and a taper of the inner surface of the gap means an increase of the diameter of the shaft towards the impeller-side end of the gap. It is preferred to provide the taper in the surface of the shaft, whereas the opening constituting the outer boundary of the gap may be cylindrical, because of ease of manufacture.

A preferred length of the gap is in the range from 1 to 2 mm, preferably 1.3 to 1.7 mm, whereas the minimum gap width may be 5 µm or less, preferably 4 µm or less, more preferably 3 µm or less, and most preferably 2 µm or less. The maximum gap width is typically located at the end of the gap opposite the impeller-side end of the gap and amounts to 15 µm or less, preferably 10 µm or less, more preferably 8 µm or less, and most preferably 6 µm or less. Most preferred is a converging gap having a maximum gap width of about 6 µm and a minimum gap width of 2 µm or less.

Furthermore, the gap may converge continuously, in particular linearly, over at least part of its length up to where the gap has its minimum width.

In a particularly preferred embodiment, at least one of the two surfaces forming the circumferential gap is made of a material having a thermal conductivity $\lambda \geq 100$ W/mK.

Making the surfaces from a material having a relatively high thermal conductivity, the temperature in the gap can be kept low, preferably at 55° C. or lower, thereby preventing denaturation of any fibrin in the blood plasma that might enter the gap despite all efforts taken.

A material of the surface or surfaces forming the gap with a thermal conductivity of 100 W/mK may be sufficient to conduct the heat away from the gap and, thus, maintain the temperature within the gap at 55° C. or below. However, the thermal conductivity is preferably at least 130 W/mK, more preferably at least 150 W/mK and most preferably at least 200 W/mK.

In order to convey the heat away from the gap into the blood, it is preferable that said gap-forming surface is in thermoconductive contact with the blood flow flowing through the pump. According to thermodynamics, flowing blood carries away heat faster than non-flowing blood. The faster the blood flow is, the more heat can be carried away by conductive thermal transfer. Blood flow velocity through the pump is generally higher than blood flow velocity outside the pump. Accordingly, for instance, the heat generated in the gap and heating up the gap-forming surfaces may be further conducted from the surface of the shaft through the shaft body into the impeller at the end of the shaft, and from there into the blood flowing along the impeller. However, since the distance for the heat to flow in an axial direction through the shaft body and further through the impeller into the blood is relatively long, it is rather preferred to conduct the heat away from the gap (in addition or only) in a radial direction, i.e. via the radial outer surface forming the gap. Carrying away the heat in a radial direction is not only preferable because of the relatively short radial distance for the heat to flow from the gap to the flowing blood, but also because it is easier to increase the thermoconductive area through which heat can be conducted in the radial direction as compared to the thermoconductive cross-sectional area of the shaft body through which heat can be conducted in the axial direction. That is, the cross-sectional area $A_{axial}$ of the shaft body is $A_{axial}=\pi d^2/4$ and the cross-sectional area $A_{radial}$ of the gap-forming radial outer surface is $A_{radial}=\pi dl$. Thus, the positive impact of increasing the diameter (e.g. to d=1 mm) of the gap is four times higher on the cross-sectional area $A_{radial}$ of the gap-forming radial outer surface than on the cross-sectional area $A_{axial}$ of the shaft body. Furthermore, increasing the length (l) of the gap has a positive impact only on the cross-sectional area $A_{radial}$ of the gap-forming radial outer surface and no effect at all on the cross-sectional area $A_{axial}$ of the shaft body. In any case, the gap should preferably be long and have a large diameter. However, since a large diameter may counter the amount of heat generated in the gap, the diameter of the gap should not be too large (preferably d about ≤1 mm). Most preferably, the thermal conductivity of both surfaces forming the gap is high, at least 100 W/mK, and in thermoconductive contact with the blood flow.

Such thermoconductive contact may be direct or indirect. Direct thermoconductive contact can be achieved if the respective thermoconductive surface forming the gap makes part of a structural element which is entirely made of said thermoconductive material and which, when the intravascular blood pump is in operation in a blood vessel of a patient, is in direct contact with the blood flow through the pump. This may be the case when the shaft and the impeller form an integral part formed from one thermoconductive material and/or when the distal end of the housing forming the through-opening for the passage of the shaft is an integral part made of a thermoconductive material.

Alternatively, indirect thermoconductive contact can be achieved if the surface or surfaces forming the gap make part of a structural element, respectively, which is entirely made of said thermoconductive material and has at least one further surface thermoconductively connected to a separate thermoconductive element which, when the intravascular blood pump is in operation in a blood vessel of a patient, is either in direct contact or via one or more further thermoconductive elements in indirect thermoconductive contact with the flowing blood, so that the heat from the gap-forming surface or surfaces can dissipate into the flowing blood by thermal conduction. Of course, the thermoconductive elements should themselves have high thermal conductivity, preferably higher than the preferred thermal conductivity of the surface or surfaces forming the gap, i.e. higher than 100 W/mK, preferably higher than 130 W/mK, more preferably higher than 150 W/mK and most preferably higher than 200 W/mK.

Since the surfaces forming the gap may preferably constitute a radial sliding bearing for the shaft, the surfaces should have very little surface roughness, preferably a surface roughness of 0.1 µm or less. While such surface roughness could be obtained with a diamond-like carbon coating (DLC), as proposed in US 2015/0051436 A1 as a coating for the shaft, it is not possible with current technologies to apply the DLC coating with such accuracy that a gap width of 2 µm or less can be achieved over the length of the gap. It is therefore preferred to make the gap-forming surface or surfaces from a material different from DLC and/or by different methods, most preferably from ceramic material, in particular from a sintered ceramic element. That is, preferably, said thermoconductive surface is not a coating on a structural element but the surface of one or more structural elements, i.e. the surface of one or more elements from which the pump is assembled.

A general problem with ceramic is that ceramic materials typically have a very low thermal conductivity. For instance, the zirconium oxide ($ZrO_2$) mentioned in US 2015/0051436 A1 has a thermal conductivity of only 2.5 to 3 W/mK. Aluminum oxide ($Al_2O_3$), which is a well-known ceramic, has a comparatively high thermal conductivity of 35 to 40 W/mK, but this is still substantially lower than the thermal conductivity of metals, such as copper. One of the very few ceramics having a substantially higher thermal conductivity is silicon carbide (SiC). Typical technical silicon carbides have a thermal conductivity of between 100 W/mK and 140 W/mK, but silicon carbides with higher thermal conductivity are likewise available. Pure silicon carbide has a thermal conductivity of 350 W/mK. Unlike other ceramics, silicon carbide is very brittle and, therefore, difficult to work with. It can easily break during manufacture and assembling. Nevertheless, for its good thermal capacity, silicon carbide is for the present purpose the preferred material for at least one of the surfaces forming the gap, preferably the radial outer surface of the gap and, because of its brittleness, rather not the shaft. Thus, the respective surface or the entire structural element forming such surface comprises or preferably consists of silicon carbide.

Where silicon carbide forms one surface of a sliding bearing, the cooperating opposite surface of the sliding bearing may essentially be of any other type of material, in particular any other type of ceramic material. A preferred ceramic material for the respective other surface is alumina toughened zirconia (ATZ) because of its high durability, which has, however, a thermal conductivity of only 25 W/mK. It is therefore preferred to make the shaft from ATZ and the sleeve in which the shaft is journaled from SiC so that the heat can easily be conducted radially outwardly away from the gap into the flowing blood.

BRIEF DESCRIPTION OF DRAWINGS

Hereinafter, the invention will be explained by way of example with reference to the accompanying drawings. The accompanying drawings are not intended to be drawn to scale. In the drawings, each identical or nearly identical component that is illustrated in various figures is represented by a like numeral. For purposes of clarity, not every component may be labelled in every drawing. In the drawings:

FIG. 1 represents the employment of a blood pump for supporting, in this particular example, the left ventricle. The blood pump comprises a catheter 14 and a pumping device 10 attached to the catheter 14. The pumping device 10 has a motor section 11 and a pump section 12 which are disposed coaxially one behind the other and result in a rod-shaped construction form. The pump section 12 has an extension in the form of a flexible suction hose 13, often referred to as "cannula". An impeller is provided in the pump section 12 to cause blood flow from a blood flow inlet to a blood flow outlet, and rotation of the impeller is caused by an electric motor disposed in the motor section 11. The blood pump is placed such that it lies primarily in the ascending aorta 15b. The aortic valve 18 comes to lie, in the closed state, against the outer side of the pump section 12 or its suction hose 13. The blood pump with the suction hose 13 in front is advanced into the represented position by advancing the catheter 14, optionally employing a guide wire. In so doing, the suction hose 13 passes the aortic valve 18 retrograde, so the blood is sucked in through the suction hose 13 and pumped into the aorta 16.

Figure 1:
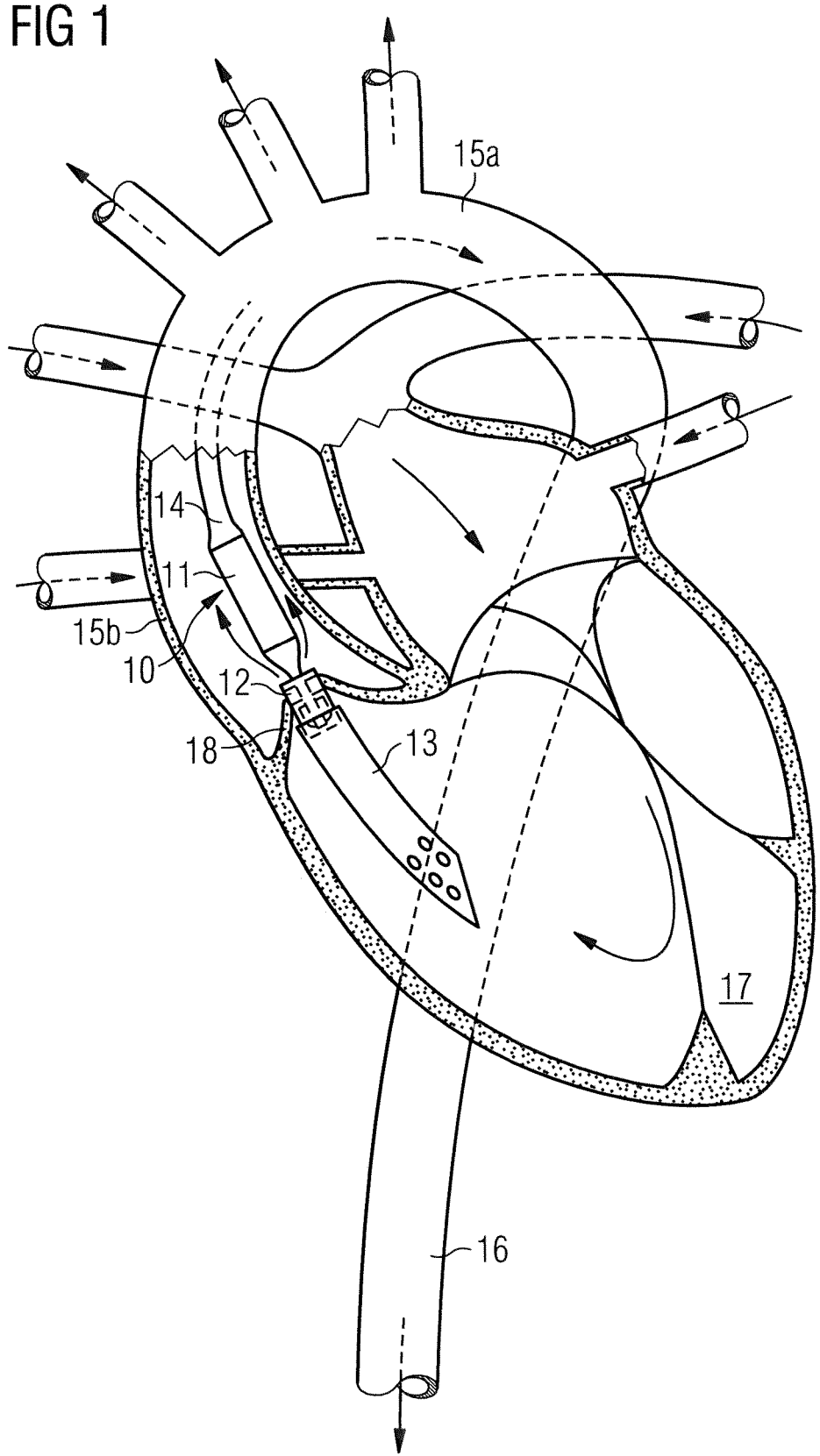
FIG. 1 is a schematic representation of an intravascular blood pump inserted before the left ventricle, with its inflow cannula positioned in the left ventricle.

The use of the blood pump is not restricted to the application represented in FIG. 1, which merely involves a typical example of application. Thus, the pump can also be inserted through other peripheral vessels, such as the subclavian artery. Alternatively, reverse applications for the right ventricle may be envisioned.

Figure 2:
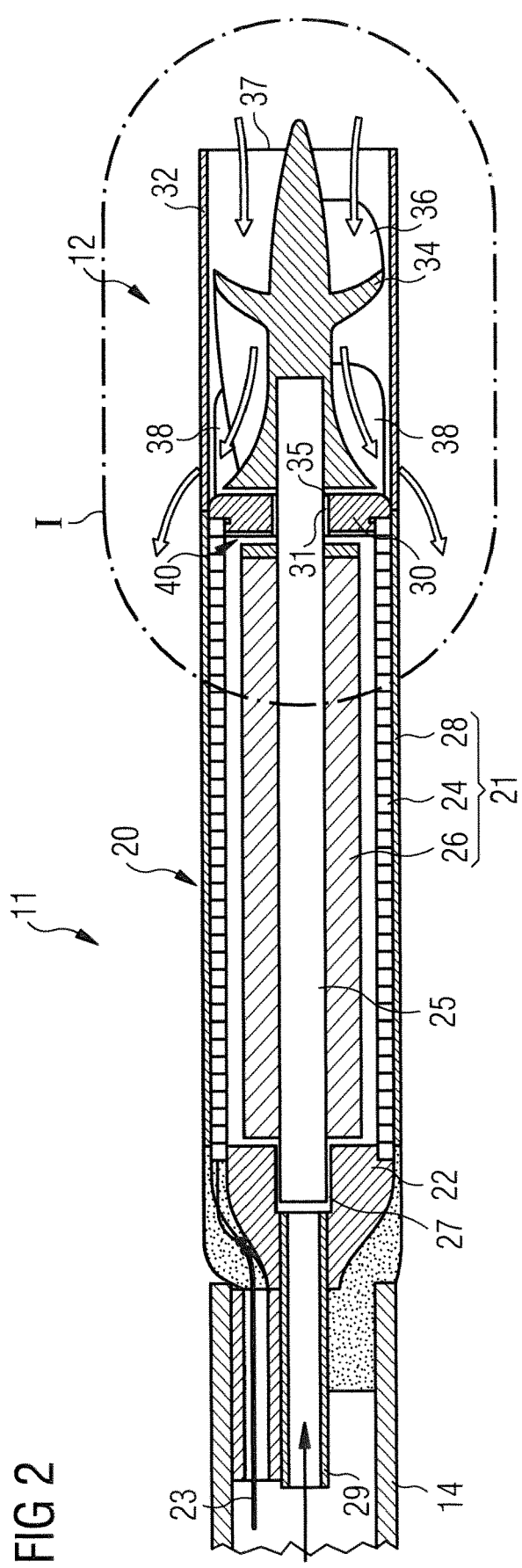
FIG. 2 is a schematic longitudinal cross-section of an exemplary prior art blood pump.
Figure 3:
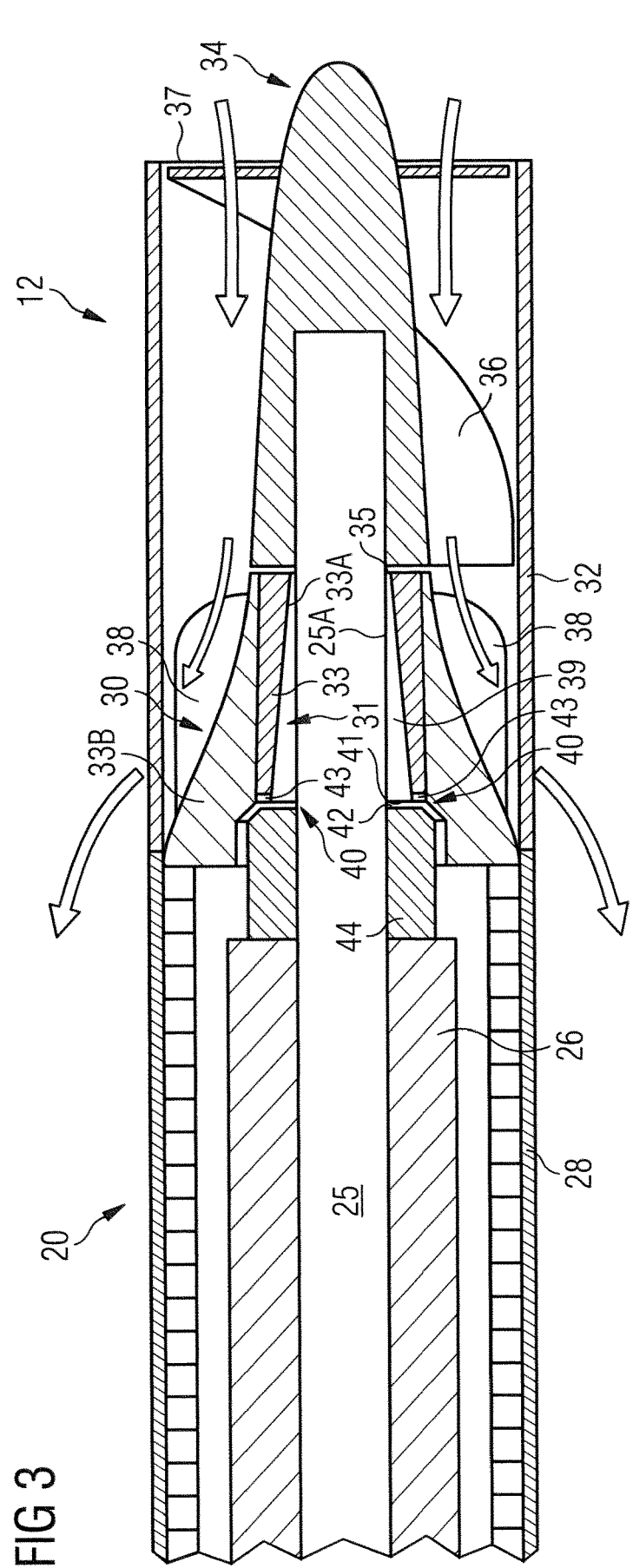
FIG. 3 is an enlarged representation of a part of the blood pump of FIG. 2, however, with a structure according to a preferred embodiment of the invention.

FIG. 2 shows an exemplary embodiment of the blood pump according to the prior art US 2015/0051436 A1, which is likewise suitable for use in the context of the present invention, except that the encircled front end marked with "I" is modified according to the invention, a preferred embodiment of such modification being shown in FIG. 3. Accordingly, the motor section 11 has an elongated housing 20 in which an electric motor 21 may be housed. A stator 24 of the electric motor 21 may have, in the usual way, numerous circumferentially distributed windings as well as a magnetic return path 28 in the longitudinal direction. The magnetic return path 28 may form an outer cylindrical sleeve of the elongate housing 20. The stator 24 may surround a rotor 26 connected to the motor shaft 25 and consisting of permanent magnets magnetized in the active direction. The motor shaft 25 may extend over the entire length of the motor housing 20 and protrude distally out of the latter through an opening 35. There, it carries an impeller 34 with pump vanes 36 projecting therefrom, which may rotate within a tubular pump housing 32 which may be firmly connected to the motor housing 20.

The proximal end of the motor housing 20 has the flexible catheter 14 sealingly attached thereto. Through the catheter 14, there may extend electrical cables 23 for power supply to and control of the electric motor 21. In addition, a purge fluid line 29 may extend through the catheter 14 and penetrate a proximal end wall 22 of the motor housing 20. Purge fluid may be fed through the purge fluid line 29 into the interior of the motor housing 20 and exit through the end wall 30 at the distal end of the motor housing 20. The purging pressure is chosen such that it is higher than the blood pressure present, in order to thereby prevent blood from penetrating into the motor housing, being between 300 and 1400 mmHg depending on the case of application.

As mentioned before, the same purged seal can be combined with a pump which is driven by a flexible drive shaft and a remote motor.

Upon a rotation of the impeller 34, blood is sucked in through the distal opening 37 of the pump housing 32 and conveyed backward within the pump housing 32 in the axial direction. Through radial outlet openings 38 in the pump housing 32, the blood flows out of the pump section 12 and further along the motor housing 20. This ensures that the heat produced in the motor is carried off. It is also possible to operate the pump section with the reverse conveying direction, with blood being sucked in along the motor housing 20 and exiting from the distal opening 37 of the pump housing 32.

The motor shaft 25 is mounted in radial bearings 27, 31 at the proximal end of the motor housing 20, on the one hand, and at the distal end of the motor housing 20, on the other hand. The radial bearings, in particular the radial bearing 31 in the opening 35 at the distal end of the motor housing, are configured as sliding bearings. Furthermore, the motor shaft 25 is also mounted axially in the motor housing 20, the axial bearing 40 likewise being configured as a sliding bearing. The axial sliding bearing 40 serves for taking up axial forces of the motor shaft 25 which act in the distal direction when the impeller 34 conveys blood from distal to proximal. Should the blood pump be used for conveying blood also or only in the reverse direction, a corresponding axial sliding bearing 40 may (also or only) be provided at the proximal end of the motor housing 20 in a corresponding manner.

FIG. 3 shows the portion marked with "I" in FIG. 2 in greater detail, yet structurally modified according to a preferred embodiment of the invention. There can be seen in particular the radial sliding bearing 31 and the axial sliding bearing 40. The bearing gap 39 of the radial sliding bearing 31 is formed, on the one hand, by the circumferential surface 25A of the motor shaft 25 and, on the other hand, by the surface 33A of a through bore in a bushing or sleeve 33 of the motor housing's 20 end wall 30 defining an outer gap diameter of about 1 mm, but the outer gap diameter may also be larger than this. In this embodiment, the bearing gap 39 of the radial sliding bearing 31 has a gap converging from proximal to distal with a minimum gap width of 2 µm or less in the area of the front end or impeller-side end 39A of the gap 39. Preferably the minimum gap width is between 1 µm and 2 µm. The maximum gap width is about 6 µm in this embodiment, but may be larger. The length of the gap may range from 1 mm to 2 mm, preferably from 1.3 mm to 1.7 mm, e.g. 1.5 mm, corresponding to the length of the radial sliding bearing 31. The surfaces forming the gap of the radial sliding bearing 31 have a surface roughness of 0.1 µm or less.

The shaft 25 is preferably made of ceramic material, most preferably from alumina toughened zirconia (ATZ) to avoid shaft fractures. ATZ has a relatively high thermal conductivity due to the aluminum which has a thermal conductivity of between 30 and 39 W/mK. The impeller 34 carried on the distal end of the shaft 25 is preferably made of a material having an even higher thermal conductivity. This way, heat generated in the very narrow gap 39 of the radial sliding bearing 31 can dissipate through the shaft 25 and the impeller 34 into the blood flowing along the outer surface of the impeller 34.

However, in an embodiment where the impeller is made of a material having low thermal conductivity, such as PEEK, or even in embodiments where the impeller is made of a material having high thermal conductivity, as suggested above, it is in any case advantageous to make the sleeve 33 in the housing's 20 end wall 30 of a material with high thermal conductivity, preferably a thermal conductivity of at least 100 W/mK, more preferably at least 130 W/mK, even more preferably at least 150 W/mK and most preferably at least 200 W/mK. In particular, the sleeve 33 may be a ceramic sleeve, more specifically made of sintered ceramic material. As a particularly preferred ceramic material, the sleeve 33 may comprise or entirely consist of SiC, because of its high thermal conductivity.

While the entire end wall 30 may be formed as an integral piece made of a highly thermoconductive material, it may be preferable to assemble the end wall 30 from the sleeve 33 and one or more radially outer elements 33B which are itself thermoconductive. This may be important in particular where the sleeve 33 is made of brittle material, such as SiC. Accordingly, the radial outer thermoconductive element 33B is thermoconductively connected to the sleeve 33 and has itself a thermal conductivity which is preferably higher than the thermal conductivity of the sleeve 33 and in any case at least 100 W/mK so as to guarantee that the heat from the sleeve 33 can dissipate through the thermoconductive element 33B into the flowing blood by thermal conduction and diffusion.

As can further be seen from FIG. 3 as compared to the prior art structure shown in FIG. 2, the axial length of the end wall 30 of the housing 20 is relatively long. More specifically, the path for the blood to flow along the outer surface of the housing's 20 end wall 30 is longer in the axial direction than in the radial direction. This provides a large surface area for heat to transfer from the housing's 20 end wall 30 into the blood flow. For instance, the blood flow may be guided outwardly along the end wall 30 of the housing 20 over a radial distance of between 0.5 and 1 mm, preferably about 0.75 mm, while flowing in an axial direction of 1.5 mm to 4 mm, preferably about 3 mm.

As regards the bearing gap of the axial sliding bearing 40, this is formed by the axially interior surface 41 of the end wall 30 and a surface 42 opposing it. This opposing surface 42 may be part of a ceramic disc 44 which may be seated on the motor shaft 25 distally of the rotor 26 and rotate with the rotor 26. A channel 43 may be provided in the bearing-gap surface 41 of the end wall 30 to ensure purge fluid flow through between the bearing-gap surfaces 41 and 42 of the axial sliding bearing 40 towards the radial sliding bearing 31. Other than this, the surfaces 41 and 42 of the axial sliding bearing 40 may be flat. The bearing gap of the axial sliding bearing 40 is very small, being a few micrometer.

When the bearing-gap surface 41 of the axial sliding bearing 40 is formed by the sleeve 33, as shown in FIG. 3, and the sleeve 33 is made of SiC, the ceramic disc 44 forming the opposing surface 42 of the axial sliding bearing 40 is preferably made of alumina toughened zirconia (ATZ). Alternatively, the opposing bearing-gap surface 42 may be DLC-coated or may likewise be made of SiC.

The pressure of the purge fluid is adjusted such that the pressure drop along the radial sliding bearing 31 is preferably about 500 mmHg or more to maintain high axial purge flow velocity (≥0.6 m/s) within the narrow 1 to 2 µm gap. The blood pump 10 can be operated with purge fluid which is free from heparin. The blood pump can even be run without any purge fluid at least for hours if the purge fails.

Figure 4A:
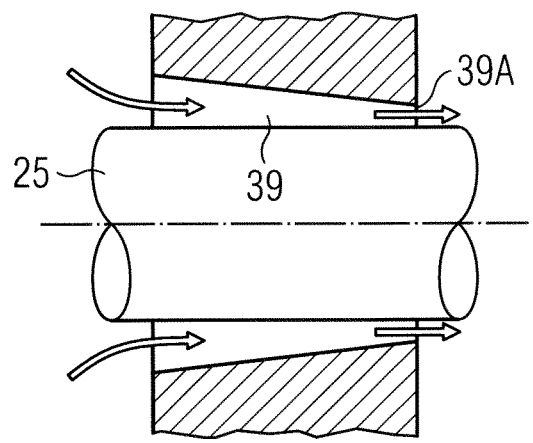
FIGS. 4A to 4I are enlarged partial views of the pump's distal radial bearing showing variations of a converging circumferential gap.
Figure 4B:
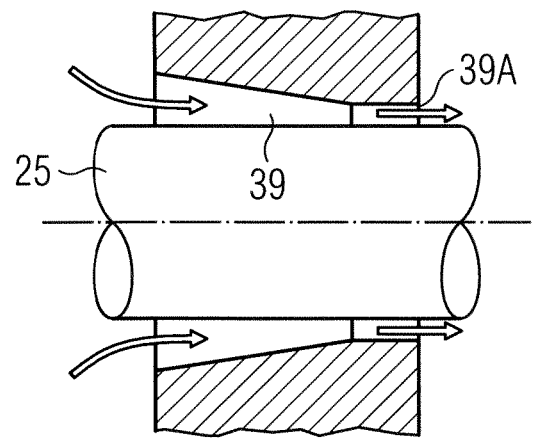
Figure 4C:
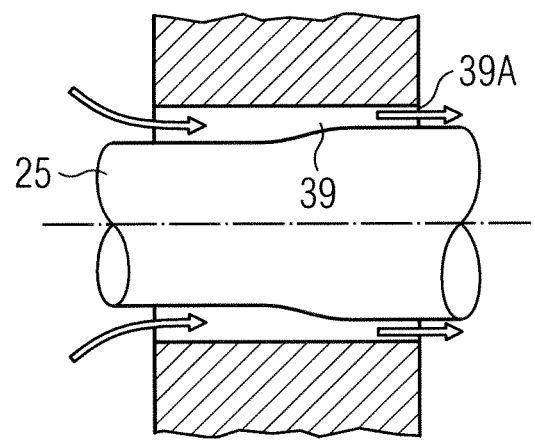

FIGS. 4A to 4C show variations of the converging circumferential gap 39 defining the radial sliding bearing 31 at the distal end of the blood pump housing 20. The arrows indicate the flow direction of the purge fluid with which the radial sliding bearing 31 is purged.

A first embodiment of the converging gap 39 is shown in FIG. 4A. Here, the gap converges continuously, more specifically linearly, from proximal to distal with the minimum gap width being located exactly at the impeller-side end 39A of the gap 39.

The gap 39 in the embodiment shown in FIG. 4B likewise converges continuously and linearly from proximal to distal towards the impeller-side end 39A of the gap 39, but the minimum gap width extends over a partial length of the gap 39 so as to form a cylindrical end section thereof. The cylindrical end section of the gap 39 as shown in FIG. 4B is less prone to wear than the pointed end section as shown in the embodiment of FIG. 4A. In both embodiments the gap may alternatively converge non-linearly, in particular convexly or, in other words, degressively from proximal to distal.

Figure 4D:
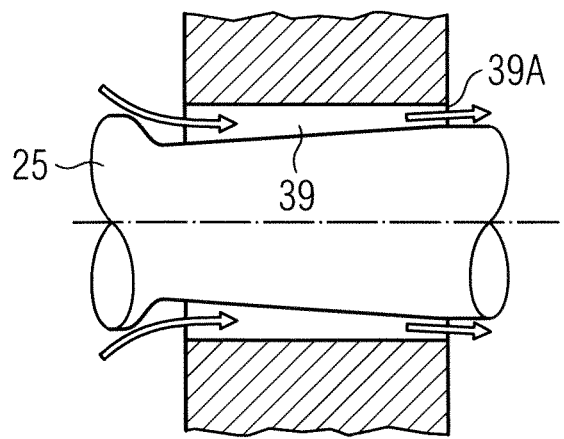

While in the embodiments shown in FIGS. 4A and 4B the convergence of the gap 39 is due to a taper of the opening 35 having a narrower diameter distal as compared to proximal, FIG. 4C and FIG. 4D relate to embodiments where the convergence of the gap 39 is realized by a taper of the shaft 25. More specifically, an outer diameter of the shaft 25 extends towards the impeller-side end 39A of the gap 39 in both cases. In FIG. 4C, the outer diameter of the shaft 25 expands from a constant diameter shaft section at the proximal side of the gap 39, which constant diameter shaft section stretches over an end of the gap 39 opposite the impeller-side end 39A of the gap 39, to a maximum outer diameter within the gap 39. In the embodiment shown in FIG. 4D, the outer diameter of the shaft has a circumferential groove, the groove likewise stretching over an end of the gap 39 opposite the impeller-side end 39A of the gap 39. In the embodiment shown, the diameter of the groove increases linearly from proximal to distal so that the minimum gap which is reached shortly before the impeller-side end 39A of the gap 39. However, instead of a linearly converging gap 39, the diameter of the shaft 25 may increase e.g. progressively towards the impeller-side end 39A of the gap 39.

The variations described in relation to the embodiments shown in FIGS. 4A to 4D may be combined in any suitable manner, i.e. the converging gap 39 may be formed by both a tapering diameter of the opening through which the shaft 25 extends and a tapering shaft 25.

Figure 4E:
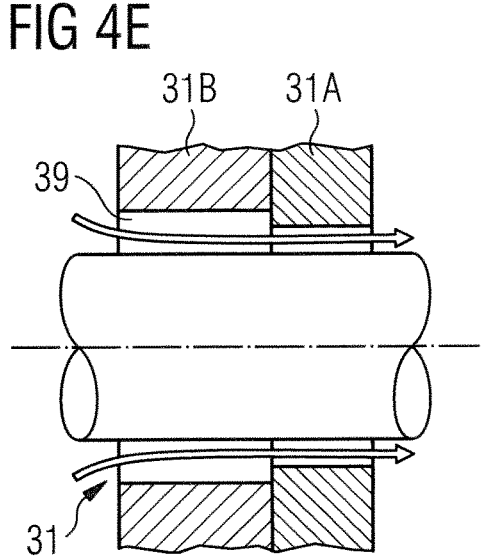
Figure 4F:
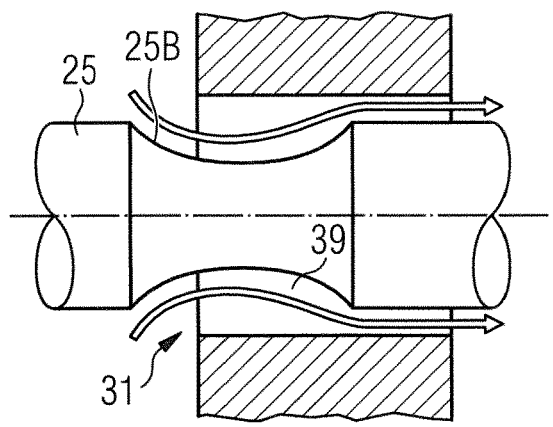
Figure 4G:
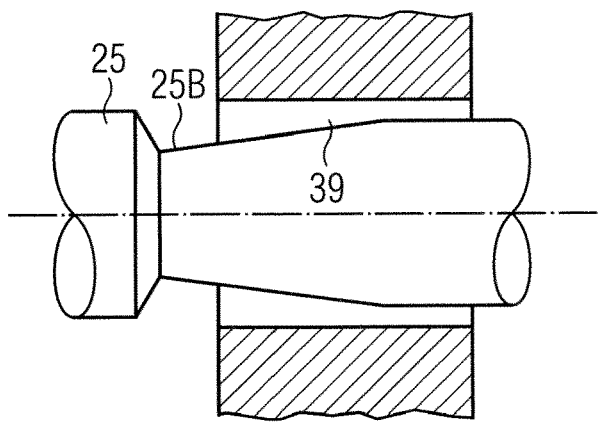
Figure 4H:
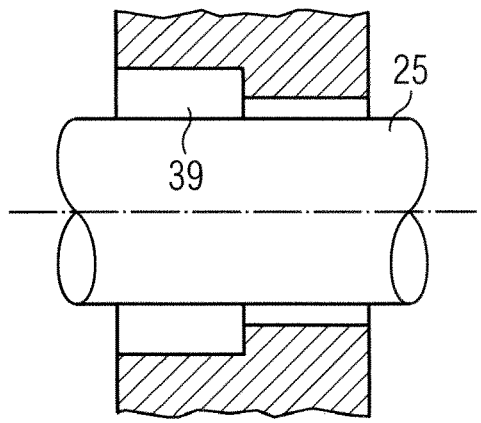
Figure 4I:
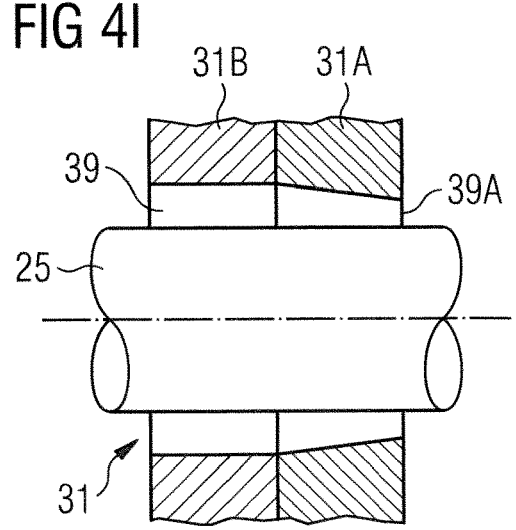

FIGS. 4E to 4I relate to embodiments of the pump's distal radial bearing 31 which are optimized regarding an easy manufacture of the converging gap 39. In FIG. 4E the bearing 31 is divided in two bearing rings 31A and 31B with the distal bearing ring 31A in contact with the blood having an opening with a smaller diameter than the opening of the proximal bearing ring 31B. In FIG. 4F the converging gap is realized by a circumferential groove 25B in the surface 25A of the shaft 25, the groove 25B having a simple curved cross section. In FIG. 4G the converging gap is likewise realized by a circumferential groove 25B in the surface 25A of the shaft 25, but here the groove 25B is such that the shaft 25 has a conical axial cross section in the region of the gap 39. In FIG. 4H the bearing 31 is formed by a stepped bore having a smaller diameter at the distal end being in contact with the blood as compared to the proximal end of the gap 39, similar to the embodiment of FIG. 4E. In FIG. 4I, again, the bearing 31 is divided in two bearing rings 31A and 31B with the distal bearing ring 31A in contact with the blood having a smaller diameter than the proximal bearing ring 31B. However, in this embodiment the proximal bearing ring 31B has a cylindrical inner surface, whereas the distal ring 31A has a conical inner diameter converging towards the impeller-side end 39A of the gap.

The invention claimed is:

1. An intravascular blood pump, comprising:
a rotatable shaft carrying an impeller; and
a housing having an opening;
wherein the shaft extends through the opening with the impeller positioned outside said housing, the shaft and the housing having surfaces forming a circumferential gap within said opening, wherein the gap has a length and a width, said width having a minimum width located somewhere within 50% of the length of the gap closest to an impeller-side end of the gap; and wherein the gap converges over at least part of its length up to where the gap has the minimum width.

2. The intravascular blood pump according to claim 1, wherein an outer diameter of the shaft expands towards the impeller-side end of the gap.

3. The intravascular blood pump according to claim 2, wherein the outer diameter of the shaft has a circumferential groove stretching over an end of the gap opposite the impeller-side end of the gap.

4. The intravascular blood pump according to claim 2, wherein the outer diameter of the shaft expands from a constant diameter shaft section stretching over an end of the gap opposite the impeller-side end of the gap to a maximum outer diameter within the gap.

5. The intravascular blood pump according to claim 1, wherein the minimum width extends over 30% or less of the length of the gap.

6. The intravascular blood pump according to claim 5, wherein the minimum width extends over not more than 20% of the length of the gap.

7. The intravascular blood pump according to claim 1, wherein the length of the gap is in the range of from 1 to 2 mm.

8. The intravascular blood pump according to claim 7, wherein the length of the gap is in the range of from 1.3 to 1.7 mm.

9. The intravascular blood pump according to claim 1, wherein the minimum width of the gap is 5 µm or less.

10. The intravascular blood pump according to claim 9, wherein the minimum width of the gap is 2 µm or less.

11. The intravascular blood pump according to claim 1, wherein the minimum width is present at the impeller-side end of the gap.

12. The intravascular blood pump according to claim 1, wherein the gap converges continuously over at least part of its length up to where the gap has the minimum width.

13. The intravascular blood pump according to claim 1, wherein the gap converges linearly over at least part of its length.

14. The intravascular blood pump according to claim 1, wherein a diameter of the opening converges towards the impeller-side end of the gap.

15. The intravascular blood pump according to claim 1, wherein a maximum width of the gap is 15 µm or less.

* * * * *